United States Patent
Lee et al.

(10) Patent No.: US 7,488,843 B1
(45) Date of Patent: Feb. 10, 2009

(54) OXIDATION PROCESS FOR AROMATIC COMPOUND

(75) Inventors: Albert Wai Ming Lee, North Point (HK); Hao He, Kowloon (HK)

(73) Assignee: Hong Kong Baptist University, Kowloon, Hong Kong SAR (CN)

( * ) Notice: Subject to any disclaimer, the term of this patent is extended or adjusted under 35 U.S.C. 154(b) by 45 days.

(21) Appl. No.: 11/930,578

(22) Filed: Oct. 31, 2007

(51) Int. Cl.
*C07C 51/16* (2006.01)

(52) U.S. Cl. .................. 562/407; 562/408; 562/409

(58) Field of Classification Search .............. 562/407, 562/408, 409
See application file for complete search history.

(56) References Cited

U.S. PATENT DOCUMENTS 5,527,956 A * 6/1996 Jones .................. 562/409

* cited by examiner

*Primary Examiner*—Sikarl A Witherspoon
(74) *Attorney, Agent, or Firm*—Leydig, Voit & Mayer, Ltd.

(57) ABSTRACT

Methylene substituted aromatic compounds can be oxidized using t-butyl hydroperoxide and microwave radiation. In particular, xylenes give primarily phthalic acids, while toluene gives benzoic acid. Other methylene substituted aromatic compounds where the methylene group is not part of a methyl group give ketones, rather than acids. For example, fluorene gives fluorenone. The process avoids the need for the presence of metals such as in catalysts or in oxidizing agents, and can be carried out using water rather than an organic solvent. Thus the process can conform with the ideals of green chemistry.

10 Claims, 1 Drawing Sheet

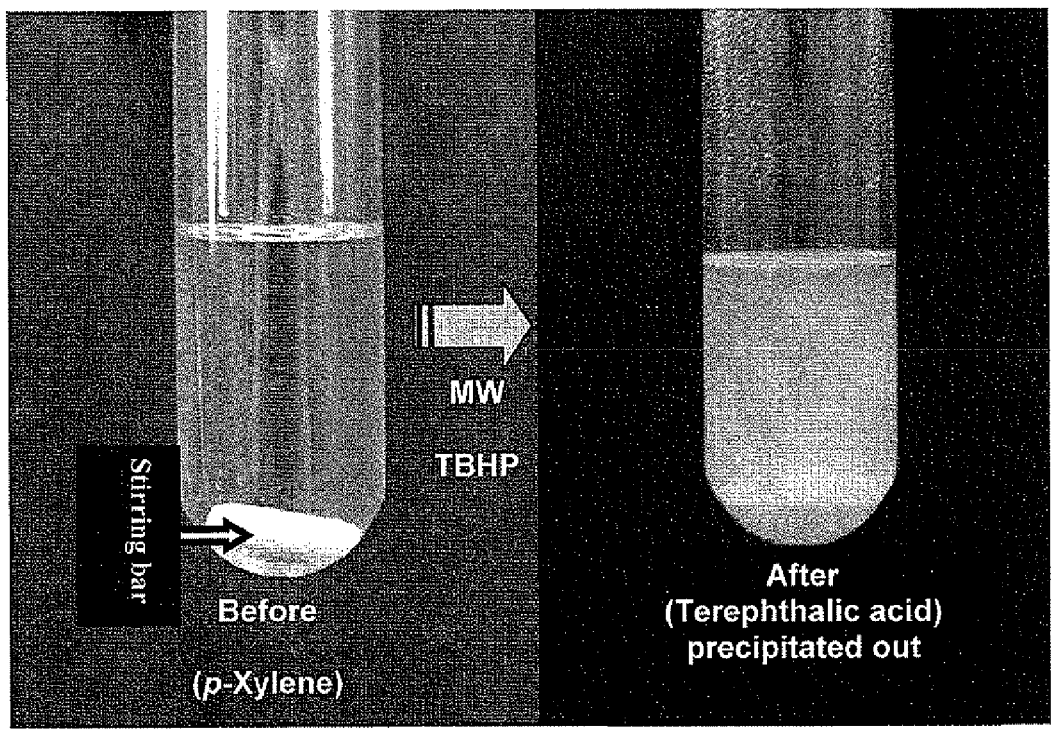

OXIDATION PROCESS FOR AROMATIC COMPOUND

The present invention relates to an oxidation process. More particularly it relates to oxidation of substituted aromatics to ketones or carboxylic acids.

BACKGROUND OF THE INVENTION

Oxidation is the core technology to convert petrochemical based materials to commodity chemicals of higher oxidation state. However, oxidation reactions present some of the greatest challenges to the environment. Many of the industrial oxidation processes involve heavy metals or corrosive reagents, and are high in energy consumption.

Selective benzylic oxidations of alkyl substituted aromatics to ketones or carboxylic acids are fundamentally important laboratory and commercial organic transformations[1,2,3]. The oxidation products are essential intermediates for the manufacture of high-value fine chemicals, agrochemicals, pharmaceuticals and high-tonnage commodities[4,5]. Such benzylic oxidations can be achieved by various oxidizing agents based on transition metals, such as permanganate and chromate. If molecular oxygen, hydrogen peroxide or hydroperoxide are used as the oxidants, metal-based catalysts either homogeneous or heterogeneous are needed[2,6].

For example, terephthalic acid is produced by oxidation of p-xylene under aggressive conditions. Terephthalic acid is ranked as one of the top 50 industrial chemicals with a global demand amounting to 40 million tonnes per year and an annual growth rate around 5 to 10%[6]. It is the key monomer of polyethylene terephthalate (PET). PET is the common material for making soda bottles and other packaging resins. Textile and synthetic fibres such as polyesters (Terylene) are also made from terephthalic acids.

In the industrial process of making terephthalic acid, p-xylene is oxidized by air in acetic acid at 200° C. and a pressure of 20 atm. The catalyst system is made of bromides of heavy metals and salts of cobalt and manganese. The reaction must be carried out in a titanium-lined reactor because the reaction mixture is highly corrosive. On the other hand, gas-phase oxidation of o-xylene to phthalic acid is carried out with fluidized-bed $V_2O_5$ based catalyst. Phthalic acid is the key precursor of many plasticizers. In all these known oxidation processes of methyl aromatics, metal based oxidizing agents or catalysts are required. If air is used as the oxidizing agent, high reaction temperature and pressure are usually involved.

In recent years, there have been considerable efforts for the development of environmentally conscious procedures for the production of carbon and aromatic feedstocks[7,8,9]. For instance, the uses of heavy metals should be avoided due to their toxicities, negative environmental impacts and the need for removal of residual metals from the reaction products. The uses of organic solvents should also be reduced, if not totally abandoned, to reduce VOC emission. This so called Green Chemistry is said to be the future of a sustainable chemical industry.

OBJECTS OF THE INVENTION

An object of this invention is to provide an oxidation process which is more environmentally acceptable, and in particular does not mandate the use of metals such as heavy metals. In a related object, the need for an organic solvent can be avoided, if desired.

SUMMARY OF THE INVENTION

We provide an oxidation procedure for oxidising methylene substituted aromatic compounds, using tert-butyl hydroperoxide (TBHP) as the oxidant and microwave radiation as energy source, to give ketones or carboxylic acids.

In particular, xylenes give phthalic acids usually in admixture with other acids, while toluene gives benzoic acid. Other methylene substituted aromatic compounds where the methylene group is not part of a methyl group give ketones, rather than acids. For example, fluorene gives fluorenone. The process avoids the need for the presence of metals such as in catalysts or in oxidizing agents, and can be carried out using water rather than an organic solvent.

SUMMARY OF THE DRAWING

The FIGURE provides photographs of p-xylene before and after oxidation using TBHP and microwave irradiation.

DETAILS OF THE INVENTION

The process typically employs an excess of TBHP. For oxidation of aromatic methylene compounds which are not aromatic methyl compounds, the molar ratio of TBHP:aromatic compound is suitably at least 2:1, such as at least 5:1; say about 10:1. For oxidation of aromatic methyl compounds, a higher ratio is desirable, preferably at least 15:1, or more preferably at least 25:1; say about 20:1 or 30:1.

The reaction temperature is ordinarily in the range of 100° C. to 220° C., such as 140° C. to 190° C., preferably 145° C. to 195° C. Such temperatures are achieved by irradiation at appropriate power and frequency.

The reaction duration is usually in from 20 minutes to 5 hours, such as 40 minutes to 4 hours, preferably about 1 hour.

In one aspect, the invention provides for oxidation of a compound of the formula I:

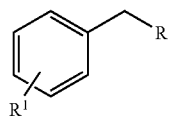

where R is a group selected from hydrogen, alkyl, and aryl; and $R^1$ is one or more substituents selected from hydrogen, alkyl, alkoxy, halo, hydroxy, amino, cycloalkyl, aryl or haloalkyl;

or R with an ortho $R^1$ forms a cyclic link that may itself be substituted or fused.

Alkyl groups preferably have 1 to 6 carbon atoms, especially 1 or 2 carbon atoms. Aryl groups and aromatic compounds are preferably hydrocarbon and are usually are phenyl. The alkyl moiety of alkoxy groups is preferably as defined. Halo groups include chloro and bromo. Amino groups can be simple amino, or primary or secondary amino groups. Cycloalkyl groups preferably have 3 to 8 carbon atoms.

There are usually 1 or 2 $R^1$ groups, preferably 1 $R^1$ group.

Preferred compounds include those where R is hydrogen, such as toluene and the three xylenes, especially p-xylene.

Other preferred compounds include diphenylmethane and ethylbenzene

When R with $R^1$ forms a cyclic link, it can be a polymethylene, such as —$(CH_2)_n$— where n is for example 2 or 3. The link may itself be fused with an aromatic ring. Examples of such compounds include fluorene and tetrahydronaphthalene.

The result of the oxidation depends on whether R is hydrogen or not.

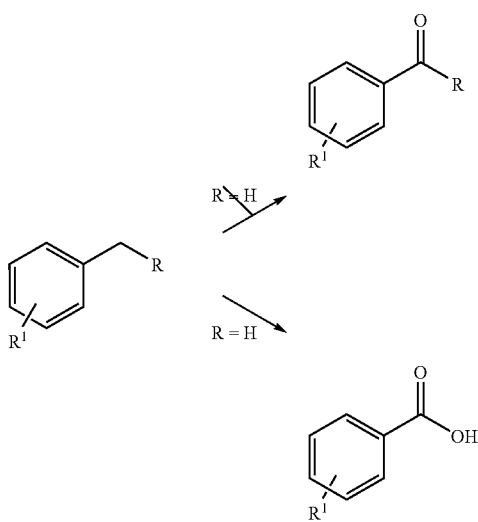

Thus, toluene yields benzoic acid. Xylene typically yields a mix of phthalic, toluic and benzoic acids. We prefer processes where the amount of phthalic acid in the mix is greater than the sum of other acid products.

Preferably the process is metal- and organic solvent-free. In particular, the process can be performed in the absence of a metal catalyst, such as a heavy metal catalyst. Furthermore, the process can be performed without organic solvent, though omission of organic solvent is not obligatory. Typically we employ aqueous TBHP, though in a less preferred aspect an organic solvent is included, especially a polar solvent such as t-butanol, nitrobenzene or acetonitrile.

In more detail, TBHP (tert-butyl hydroperoxide), such as 70% aqueous TBHP, with microwave irradiation for example at 2450 Mhz can give a green oxidation protocol for alkyl substituted aromatics. Methyl aromatics (toluenes and xylenes) can be oxidized directly to the industrially important carboxylic and dicarboxylic acids. Addition of a tiny amount (0.1 to 5%, such as 1 to 4%, preferably say about 2%) of ionic liquid and/or simultaneous cooling can improve the efficiency of the oxidation. For other alkyl substituted aromatics and related compounds, ketones are obtained in good yields. The reaction medium is preferably water. No organic solvents, metal based reagents or metal based catalysts are needed.

TBHP is an inexpensive oxidant widely used in industries[10,11]. As compared to concentrated hydrogen peroxide, TBHP is quite stable towards thermal decomposition. Actually, 70% aqueous TBHP constitutes a bulk organic chemical and has been certified for truck shipment in many countries.

Microwave assisted organic synthesis is a fast growing research area[12-16]. The technique was first recognized as a method for reducing reaction time, commonly by orders of magnitude, and for clean reaction with increasing yields of products. In addition, it also provides opportunities for new reactions which are otherwise not feasible by conventional heating methods[15]. An analogy was made that microwave reactions will be the "Bunsen burners of the 21$^{st}$ century"[12,17].

EXAMPLES OF THE INVENTION

Methods

Experiments with 0.2-0.5 mmole of substrates were conducted using a CEM Discover Unit (CEM Corporation, NC, USA) in 10 mL glass vessels sealed with rubber septa in stirred mode with or without simultaneous cooling. A targeted temperature together with a maximum microwave power (250 and 80 W respectively for reactions without or with ionic liquid) was set. The targeted temperature was reached within a few minutes. During the cause of a reaction, the microwave power as well as the pressure (60 to 240 psi) varied.

For the oxidation of toluene, a convenient NMR method was developed to monitor the reactions. A sample of the reaction mixture was withdrew and diluted with CDCl$_3$. After treated with D$_2$O, the $^1$H NMR (270 MHz) spectrum was recorded. The percentage conversion can be calculated from the integrations of the well resolved aromatic proton signals of benzoic acid (7.41-7.47, 7.54-7.57 and 8.05-8.08 ppm for the meta-, para- and ortho-protons respectively) and the methyl signal (2.35 ppm) of toluene.

In a preferred aspect, the oxidations of this invention are as shown in Scheme 1:

Scheme 1
Benzylic oxidation of alkyl substituted aromatics

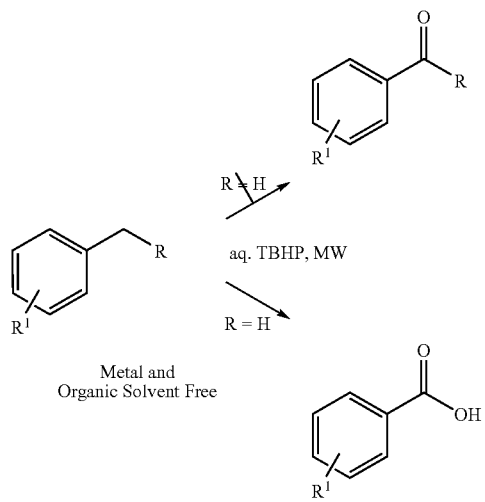

Example 1

We initially studied oxidation of methylene substituted benzylic aromatics to ketones (Scheme 1, R≠H). When a mixture of fluorene with 10 equivalents 70% aqueous TBHP was irradiated with microwave in a sealed vessel for 10 minutes (250 W, 170° C.), an almost quantitative yield of fluorenone was isolated (Table 1). As a control experiment, when we simply refluxed the same reaction mixture by conventional oil bath heating for 8 hours, only a trace amount of fluorenone could be detected by TLC. Oxidation of another substrate with a doubly activated benzylic position, diphenylmethane, also afforded benzophenone in high yield. For the mono-activated methylene units, ethylbenzene to acetophenone and tetrahydronaphthalene to alpha-tetralone, the oxidations under this green protocol also went smoothly. The results are summarized in Table 1.

TABLE 1

TBHP Oxidation of Alkyl Substituted Aromatics to Ketones under Microwave Irradiation

| Run | Substrate | Conditions | Product | yield |
|---|---|---|---|---|
| 1 | 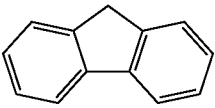 | 170° C., 10 min | 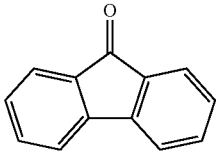 | 98% |
| 2 | 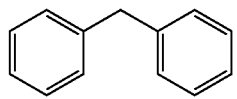 | 180° C., 30 min | 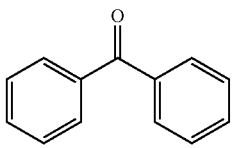 | 85% |
| 3 | 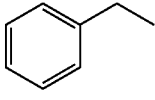 | 180° C., 30 min | 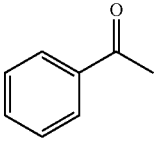 | 77% |
| 4 | 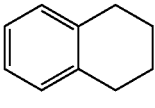 | 170° C., 30 min | 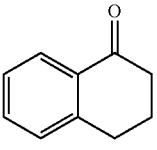 | 53% |

Example 2

With the preliminary success in the oxidation of the methylene benzylic units, we then turned to a more challenging oxidation of methyl substituted aromatics.

Oxidation of toluene to benzoic acid was first used as the model study. With six equivalents of 70% aqueous TBHP (2 folds in excess), toluene was converted in 9.1% to benzoic acid under microwave irradiation at 160° C. for 1 hr (Run 1, Table 2). It is well documented that solvents with high dielectric constants would enhance the microwave heating effect. When the oxidation reactions were carried out in tert-butanol, nitrobenzene or acetonitrile (Runs 2, 3, 4) as the co-solvents, the percentage conversions were increased to 20-27%. We also explored the uses of other TBHP formulations such as TBHP in isooctane and toluene[18,19]. Oxidation can still take place but the results are inferior to the use of aqueous TBHP.

As a control experiment, we carried out the oxidation at reflux (130° C.) by conventional heating for 7 hours. No benzoic acid could be detected from the reaction mixture. In addition, the microwave reactions have to be carried out in sealed vessels. No benzoic acid could be detected when the reaction was carried out with microwave heating in an open vessel at refluxing temperature of 104-114° C.

TABLE 2

TBHP Oxidation of Toluenes to Benzoic Acids under Microwave Irradiation

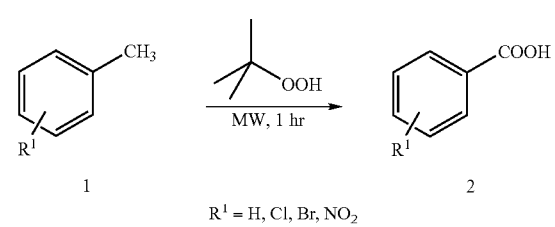

$R^1$ = H, Cl, Br, $NO_2$

| Run | G | Toluene/TBHP | Conditions | Conversion |
|---|---|---|---|---|
| 1 | H | 1:6 | Neat, 160° C. | 9.1% |
| 2 | H | 1:6 | t-BuOH, 160° C. | 20% |
| 3 | H | 1:6 | $C_6H_5NO_2$, 160° C. | 26% |
| 4 | H | 1:6 | $CH_3CN$, 160° C. | 27% |
| 5 | H | 1:6 | 2% Ionic Liquid, 160° C. | 29% |
| 6 | H | 1:20 | 2% Ionic Liquid, 150° C. | 41% |
| 7 | H | 1:20 | 2% Ionic Liquid, 150° C. with simultaneous cooling | 69% |
| 8 | H | 1:20 (1 mmol) | 2% Ionic Liquid, 150° C., 2 hr with simultaneous cooling | 94% |

TABLE 2-continued

TBHP Oxidation of Toluenes to Benzoic Acids under Microwave Irradiation

R¹ = H, Cl, Br, NO₂

| Run | G | Toluene/TBHP | Conditions | Conversion |
|---|---|---|---|---|
| 9 | o-Cl | 1:20 | 2% Ionic Liquid, 150° C. with simultaneous cooling | 46% |
| 10 | m-Cl | 1:20 | 2% Ionic Liquid, 150° C. with simultaneous cooling | 50% |
| 11 | p-Cl | 1:20 | 2% Ionic Liquid, 150° C. with simultaneous cooling | 57% |
| 12 | p-Br | 1:20 | 2% Ionic Liquid, 150° C. with simultaneous cooling | 51% |
| 13 | o-NO₂ | 1:20 | 2% Ionic Liquid, 150° C. with simultaneous cooling | 39% |
| 14 | p-OEt | 1:20 | 150° C., with simultaneous cooling | 80% |

Recently, it has been reported that addition of a small quantity of an ionic liquid can greatly increase the heating efficiency of a microwave reaction[20-22]. To improve the yield of toluene oxidation, the TBHP oxidation was carried out with 2% of 1-butyl-3-methylimidazolium tetrafluoroborate. The conversion increased to 29% as compared to 9.1% without the ionic liquid (Run 5 vs. 1).

In the $^1$H NMR spectra of all the crude reaction mixtures, we constantly observed two mysterious singlets at 2.17 and 3.46 ppm. These NMR peaks correspond to the methyl groups of acetone and methanol respectively. We speculated that TBHP is decomposed to acetone and methanol under the reaction conditions. To confirm this, a sample of 70% TBHP was heated at 160° C. under microwave irradiation for half hour. The $^1$H NMR spectra of the reaction mixture confirmed our speculation.

Two proposed mechanisms of this decomposition of TBHP are outlined in scheme 2. Similar to the thermal decomposition of cumene hydroperoxide in acidic medium, the ionic pathway involves the breakage of the weak peroxide bond followed by a methyl migrating to the electron deficient peroxide oxygen. Alternatively, a free radical mechanism can also account for the observation.

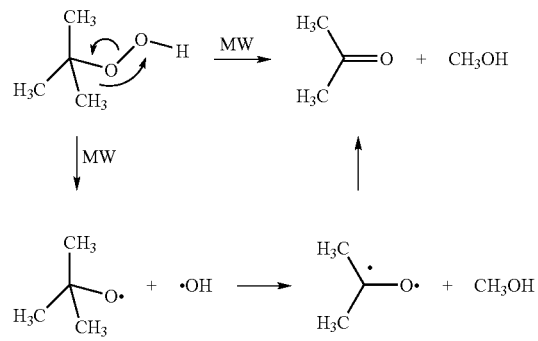

Scheme 2 Decomposition of TBHP under Microwave Irradiation

With this decomposition in mind, we increased the amount of TBHP to 20 equivalents. The conversion increased up to 41% (Run 6).

With the uses of ionic liquids, the heating was so efficient that the reaction mixture could be easily overheated within a few seconds. Therefore, the microwave power cannot be set too high (80 W vs. 250 W for experiments without ionic liquid). In addition, the microwave power drop to a rather low level (around 30 W) after the preset temperature had been reached. In order to maintain a reasonable level of microwave energy to sustain the reaction, we tried out an idea reported recently in literature[23]. A steam of compressed air or nitrogen at room temperature was passed over the reaction vessel during the microwave irradiation.

With the use of ionic liquid coupled with simultaneous cooling, the microwave power can be maintained between 70 to 40 W within the cause of the reaction (1 hr). The percentage conversion was increased to 69% (Run 7). To drive the toluene oxidation to completion, the microwave reaction (1 mmol of toluene with 20 mmol of 70% TBHP and 67 mg of 1-butyl-3-methylimidazolium tetrafluoroborate) (Run 8) was run for 2 hrs with simultaneous cooling. 94% conversion was achieved. After simple workup and recrystallization, benzoic acid was isolated in good yields.

The oxidation of substituted toluenes was also performed and the results were listed in table 2 (Runs 9-13). It is apparent that electron withdrawing substituents slow down the oxidation process. By further lowering the temperature of the cooling gas to −20° C. (from a tank of high pressure liquid nitrogen), the efficiency of the TBHP direct oxidation was only slightly improved.

A proposed free radical mechanism of this microwave assisted direct oxidation is depicted in scheme 3. Upon microwave irradiation, we hypothesise that TBHP is broken down into t-butoxide and hydroxyl radicals. Abstraction of a hydrogen radical from toluene afforded a benzyl radical which combines with a hydroxyl radical to yield benzyl alcohol. Further oxidation could lead to benzaldehyde (or its hydrate) then benzoic acid. In fact, if we limited the amount of TBHP to 4 equivalents, a tiny amount of benzaldehyde was detected in the $^1$H NMR spectra of the reaction mixture.

Scheme 3 Mechanism of Microwave-Assisted TBHP Oxidation

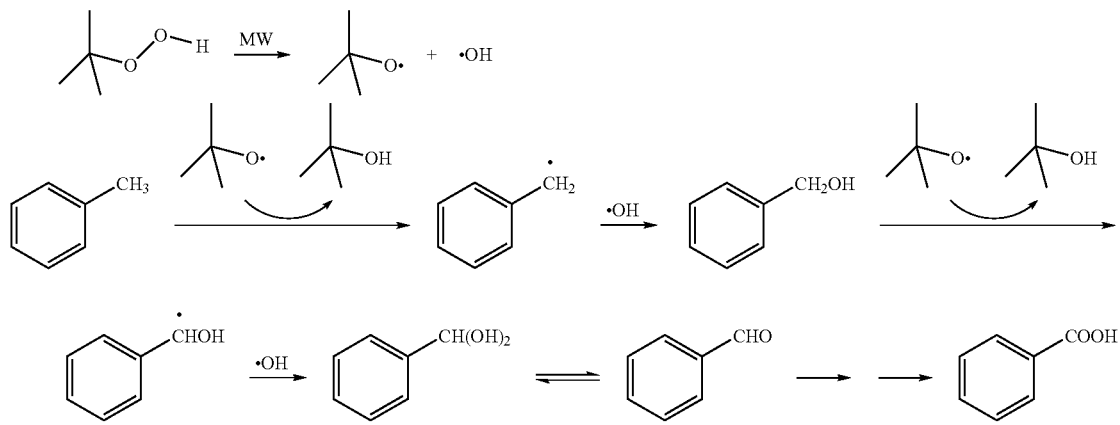

Direct oxidation of the three xylene isomers with 30 equivalents (5 folds in excess) of 70% aqueous TBHP under simultaneous cooling were also carried out as shown in scheme 4.

Scheme 4 TBHP Oxidation of Xylenes under Microwave Irradiation

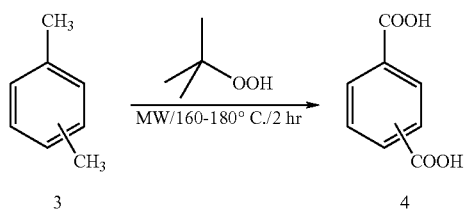

| | | |
|---|---|---|
| p-CH$_3$ | terephthalic acid | 4a |
| m-CH$_3$ | isophthalic acid | 4b |
| o-CH$_3$ | phthalic acid | 4c |

Results are summarized in Table 4. The use of ionic liquid is not crucial in these cases. The oxidation of xylenes is probably a stepwise process. Various amounts of toluic acids (methylbenzoic) were also obtained in the crude reaction mixtures. This is in line with the fact that the ease of oxidation of substituted methylbenzene parallels the electron density of the aromatic ring (entries 9-13 of table 2). Once one of the methyl groups of xylene is oxidized, the oxidation of the remaining methyl group is deactivated by the electron-withdrawing effect of the carboxyl group[24]. To our surprise, 5 to 10% of benzoic acid was also detected.

Despite the oxidation of xylene isomers yielding a mixture of products, the isolations of two of the products are still straight forward. In the case of p- and m-xylene, the oxidized benzenedicarboxylic acids (terephthalic 4a and isophthalic 4b) precipitated out from the reaction mixtures (see Supplementary Information). After filtration and recrystallization, purified terephthalic and isophthalic acids can be obtained in moderate yields.

TABLE 4

| | Yield | | |
|---|---|---|---|
| Xylene | Phthalic (Crude/Isolated) | Toluic | Benzoic |
| p- | 42%/37% | 26% | 9% |
| m- | 46%/38% | 26% | 10% |
| o- | 37%/33% | 24% | 5% |

In summary, this is the first report of direct microwave assisted oxidation of alkyl aromatics with TBHP without any metal catalyst. This oxidation of alkyl substituted aromatics to ketones, mono- and dicarboxylic acids can also be an environmental friendly green chemical process. It is performed in the absence of heavy metal, and optionally also in the absence of organic solvent. The solvent need only be water[16,25-27] that comes with TBHP. A small amount of ionic liquid could be used in the oxidation of toluenes, which is also viewed as a "green" reagent[28-30]. Finally, focused microwave is also a highly efficient "green" energy source as compared to conventional heating[31,32].

The oxidation of xylene isomers to the corresponding phthalic acids open up a green alternative to the synthesis of these economically important fine chemicals. In order to be commercial viable, we are aware that the yields might need to be improved. Using a continuous flow reactor[33,34] may be a possibility. Under a continuous flow system, the precipitated out diacid can be filtered off and the solutions recycled back to the microwave reaction. Work along these lines and applying this green oxidation protocol to other organic compounds is in progress.

REFERENCES

1. Hudlicky, M. *Oxidation in Organic Chemistry* (American Chemical Society, Washington, D.C., 1990).
2. Hughes, M. D., Xu, Y.-J., Jenkins, P., McMorn, P., Landon, P., Enache, D. I., Carley, A. F., Attard, G. A., Hutchings, G. J., King, F., Stitt, E. H., Johnston, P., Griffin, K. & Kiely, C. J. Tunable gold catalyst for selective hydrocarbon oxidation under mild conditions. *Nature* 437, 1132 (2005).
3. Bonvin, Y., Callens, E., Larrosa, I., Henderson, D. A., Oldham, J., Burton, & A. J., Barrett, A. G. M. Bismuthcatalyzed benzylic oxidation with tert-butyl hydroperoxide. *Organic Letters* 7, 4549 (2005).
4. Sheldon, R. A. & Bekkum, H. *Fine Chemicals Through Heterogeneous Catalysis*, Chapter 9 (Wiley-VCH, Weinheim, 2001).
5. Wittcoff, H. A., Reuben, B. G. & Plotkin, J. S. *Industrial Organic Chemicals* (Wiley, New Jersey, ed., 2004).
6. Weissermel, K. & Arpe, H.-J. *Industrial Organic Chemistry* (Wiley-VCH, Weinheim, ed. 4, 2003).
7. Poliakoff, M., Fitzpatrick, J. M., Farren, T. R. & Anastas, P. T. Green chemistry: science and politics of change. *Science* 297, 807 (2002).
8. An example for green production of adipic acid: Sato, K., Aoki, M. & Noyori, R. A 'green' route to adipic acid: direct oxidation of cyclohexenes with 30 percent hydrogen peroxide. *Science* 281, 1646 (1998).
9. Noyori, R., Aoki, M. & Sato, K. Green oxidation with aqueous hydrogen peroxide. *Chem. Commun.* 1977-1986 (2003).
10. Sharpless, K. B. & Verhoeven, T. R. Metal-catalyzed, highly selective oxygenations of olefins and acetylenes with tert-butyl hydroperoxide. Practical considerations and mechanisms. *Aldrichim. Acta.* 12, 63 (1979).
11. Sheldon, R. A. in *The Chemistry of Peroxides* (ed Patai, S.) (Wiley, New York, 1983)
12. For a recent review see: Kappe, C. O. Controlled microwave heating in modern organic synthesis. *Angew. Chem., Int. Ed.* 43, 6250 (2004).
13. Lidstrom, P. & Tierney, J. P., Eds. *Microwave-Assisted Organic Synthesis* (Blackwell, Oxford, 2005).
14. Loupy, A., Ed. *Microwave in Organic Synthesis* (Wiley-VCH: Weinheim, 2002).
15. Miyazawa, A., Tanaka, K., Sakakura, T., Tashiro, M., Tashiro, H., Prakash, G. K. S. & Olah, G. A. Microwave-assisted direct transformation of amines to ketones using water as an oxygen source. *Chem. Commun.* 2104 (2005).
16. Leadbeater, N. E. Fast, easy, clean chemistry by using water as a solvent and microwave heating: the Suzuki coupling as an illustration. *Chem. Commun.* 2881 (2005).
17. The term was first coined by Bose, A. K.: Bose, A. K., Banik, B. K., Lavolinskaia, N., Jayaraman, M. & Manhas, M. S. MORE chemistry in a microwave. *Chemtech,* 27, 18 (1997).
18. Katsuki, T. & Martin, V. in *Organic Reactions* (ed Paquette, L. A.) Vol 48, pp1-299 (1996).
19. Hanson, R. M. & Sharpless, K. B. Procedure for the catalytic asymmetric epoxidation of allylic alcohols in the presence of molecular sieves *J. Org. Chem.* 51, 1922 (1986).
20. Ley, S. V., Leach, A. G. & Storer, R. I. A polymer-supported thionating reagent. *J. Chem. Soc. Perkin Trans.* 1 358 (2001).
21. Leadbeater, N. E. & Torenius, H. M. A study of the Ionic liquid mediated microwave heating of organic solvents. *J. Org. Chem.* 67, 3145 (2002).
22. Leadbeater, N. E., Torenius, H. M. & Tye, H. Ionic liquids as reagents and solvents in conjunction with microwave heating: rapid synthesis of alkyl halides from alcohols and nitrites from aryl halides. *Tetrahedron* 59, 2253 (2003).
23. Arvela, R. K. & Leadbeater, N. E. Suzuki coupling of aryl chlorides with phenylboronic acid in water, using microwave heating with simultaneous cooling. *Organic Letters* 7, 2101 (2005) and references therein.
24. Parshall, G. W. & Ittel, S. D. *Homogeneous Catalysis* (Wiley, New York, ed. 2, 1992).
25. Li, C.-J. & Chen, L. Organic chemistry in water. *Chem. Soc. Rev.* 35, 68-82 (2006).
26. Lindström, U. M. & Andersson, F. Hydrophobically directed organic synthesis. *Angew. Chem. Int. Ed.* 45, 548-551 (2006).
27. Narayan, S., Muldoon, S., Finn, M. G., Fokin, V. V., Kolb, H. C. & Sharpless, K. B. "On water": unique reactivity of organic compounds in aqueous suspension. *Angew. Chen, Int. Ed.* 44, 3275 (2005)
28. Rogers, R. D. & Seddon, K. R. Eds. *Ionic Liquids as Green Solvents* (ACS Symposium Series 856, American Chemical Society, Washington D.C., 2003)
29. Rogers, R. D. & Seddon, K. R. Eds. *Ionic Liquids Industrial Applications to Green Chemistry* (ACS Symposium Series 818, American Chemical Society, 2002).
30. Wasserscheid, P. & Welton, T. Eds. *Ionic Liquids in Synthesis* (Wiley-VCH, Weinheim, 2003)
31. Nüechter, M., Ondruschka, B., Bonrath, W. & Gum, A. Microwave assisted synthesis—a critical technology overview. *Green Chem.* 6, 128 (2004).
32. Chark, J. & Macquarie, D. Eds *Handbook of Green Chemistry and technology* (Blackwell, Oxford, 2002).
33. Corner, E. & Organ, M. G. A Microreactor for microwave-assisted capillary (continuous flow) organic synthesis. *J. Am. Chem. Soc.* 127, 8160 (2005).
34. Bagley, M. C., Jenkins, R. L., Lubinu, M. C., Mason, C. & Wood, R. A simple continuous flow microwave reactor. *J. Org. Chem.* 70, 7003 (2005).

We claim:

1. A process for oxidation of a methyl or methylene substituted aromatic compound, which comprises oxidizing said methyl or methylene substituted aromatic compound using t-butyl hydroperoxide and microwave radiation.

2. The process of claim 1, wherein said oxidation is carried in an aqueous system.

3. The process of claim 2, wherein said oxidation is carried out in the absence of a metal-based catalyst.

4. The process of claim 2, wherein said oxidation is carried out in the absence of a metal-based oxidizing agent.

5. A process for oxidation of an aromatic methyl compound to give an aromatic carboxylic acid, which process comprises irradiating said aromatic methyl compound with microwave radiation while contacting said aromatic methyl compound with t-butyl hydroperoxide.

6. The process of claim 5, wherein said aromatic methyl compound is toluene and said acid is benzoic acid.

7. The process of claim 5, wherein said aromatic methyl compound is o-xylene and said acid is phthalic acid.

8. The process of claim 5, wherein said aromatic methyl compound is m-xylene and said acid is isophthalic acid.

9. The process of claim 5, wherein said aromatic methyl compound is p-xylene and said acid is terephthalic acid.

10. A process for oxidation of an aromatic methylene compound, said aromatic methylene compound not being an aromatic methyl compound, to give an aromatic ketone, which process comprises irradiating said aromatic methylene compound with microwave radiation while contacting said aromatic methylene compound with t-butyl hydroperoxide.

* * * * *